(12) United States Patent
Zhu et al.

(10) Patent No.: US 11,938,222 B2
(45) Date of Patent: Mar. 26, 2024

(54) PREGABALIN SUSTAINED RELEASE COMPOSITION AND METHOD FOR PREPARING THE SAME

(71) Applicant: Beijing Tide Pharmaceutical Co., Ltd., Beijing (CN)

(72) Inventors: Zhaolu Zhu, Beijing (CN); Yun Wu, Beijing (CN); Di Lu, Beijing (CN); Yanping Zhao, Beijing (CN); Liying Zhou, Beijing (CN); Yanan Liu, Beijing (CN)

(73) Assignee: BEIJING TIDE PHARMACEUTICAL CO., LTD., Beijing (CN)

( * ) Notice: Subject to any disclaimer, the term of this patent is extended or adjusted under 35 U.S.C. 154(b) by 0 days.

(21) Appl. No.: 16/618,756

(22) PCT Filed: Jun. 12, 2019

(86) PCT No.: PCT/CN2019/090933
§ 371 (c)(1),
(2) Date: Dec. 2, 2019

(87) PCT Pub. No.: WO2019/238068
PCT Pub. Date: Dec. 19, 2019

(65) Prior Publication Data
US 2021/0369621 A1   Dec. 2, 2021

(30) Foreign Application Priority Data

Jun. 13, 2018 (CN) .......................... 201810608326.0
Oct. 16, 2018 (CN) .......................... 201811202248.0

(51) Int. Cl.
*A61K 9/20* (2006.01)
*A61K 31/197* (2006.01)

(52) U.S. Cl.
CPC .......... *A61K 9/2054* (2013.01); *A61K 9/2009* (2013.01); *A61K 9/2018* (2013.01); *A61K 9/2027* (2013.01); *A61K 9/2031* (2013.01); *A61K 9/2059* (2013.01); *A61K 31/197* (2013.01)

(58) Field of Classification Search
CPC ................ A61K 9/2054; A61K 9/2009; A61K 9/2018; A61K 9/2027; A61K 9/2031; A61K 9/2059; A61K 31/197
See application file for complete search history.

(56) References Cited

U.S. PATENT DOCUMENTS

| | | | |
|---|---|---|---|
| 6,197,819 B1 | 3/2001 | Silverman et al. | |
| 8,945,620 B2 | 2/2015 | Bockbrader et al. | |
| 9,144,559 B2 | 9/2015 | Bockbrader et al. | |
| 10,022,447 B2 | 7/2018 | Bockbrader et al. | |
| 2013/0078290 A1* | 3/2013 | Pilgaonkar | A61K 9/2027 514/561 |
| 2013/0280324 A1* | 10/2013 | Jain | A61K 9/0002 514/561 |
| 2013/0303618 A1* | 11/2013 | Bockbrader | A61P 25/18 514/561 |
| 2014/0161880 A1* | 6/2014 | Woo | A61K 9/2027 514/561 |
| 2015/0250733 A1* | 9/2015 | Odidi | A61K 9/2886 514/561 |
| 2017/0172929 A1* | 6/2017 | Ahn | A61K 47/10 |
| 2017/0239203 A1* | 8/2017 | Lu | A61P 25/00 |
| 2019/0099376 A1* | 4/2019 | Kim | A61K 9/205 |
| 2019/0298675 A1* | 10/2019 | Sela | A61K 9/5047 |

FOREIGN PATENT DOCUMENTS

| | | |
|---|---|---|
| CN | 101330907 A | 12/2008 |
| CN | 102793685 A | 11/2012 |
| CN | 103159636 A | 6/2013 |
| CN | 103702664 A | 4/2014 |
| CN | 104546817 A | 4/2015 |
| CN | 104592049 A | 5/2015 |
| CN | 104840443 A | 8/2015 |
| CN | 104906064 A | 9/2015 |
| CN | 105434395 A | 3/2016 |
| CN | 105520918 A | 4/2016 |
| CN | 106163566 A | 11/2016 |
| WO | 2011053003 A3 | 9/2011 |
| WO | 2012035559 A3 | 6/2012 |
| WO | 2013114283 A1 | 8/2013 |
| WO | 2016062182 A1 | 4/2016 |

OTHER PUBLICATIONS

China Patent Office, CN 201811202248.0, First Office Action, dated Oct. 9, 2021, 9 pages.
China Patent Office; CN 201980014023.9, First Office Action; dated Nov. 24, 2021, 7 pages.
Wei et al. "Pharmaceutics," Henan Science and Technology Press, ISBN 978-7-5349-5936-3, 2012, 3 pages.
Fu, et al., "Pharmaceutical Excipients," China Press of Traditional Chinese Medicine, Oct. 2008, 132-133, 4 pages.
Zhu et al., "Pharmaceutics," Fourth Military Medical University Press. Aug. 2007, p. 168, 3 pages.

\* cited by examiner

*Primary Examiner* — Robert A Wax
*Assistant Examiner* — Olga V. Tcherkasskaya
(74) *Attorney, Agent, or Firm* — Umberg Zipser LLP (57) ABSTRACT

The present application relates to a pregabalin sustained release composition, comprising: (a) an active ingredient; (b) a matrix-forming agent; (c) a swelling agent; (d) a gelling agent; and optionally a filler. The pregabalin sustained release composition provided in the present application can rapidly swell in volume when exposed to aqueous medium until exceeding the dimeter of human gastric pyloric (13 mm). It thereby prolongs the gastric emptying time to increase the retention time of pregabalin in the stomach and enhances absorption of pregabalin in the small intestine and ascending colon. Moreover, the pregabalin sustained release composition provided herein achieves a sustained release for 24 h, which allows QD (once a day) administration, reduces administration number, and improves patient compliance.

11 Claims, 2 Drawing Sheets

PREGABALIN SUSTAINED RELEASE COMPOSITION AND METHOD FOR PREPARING THE SAME

CROSS-REFERENCE TO RELATED APPLICATION(S)

The present application claims the priority of International Application No. PCT/CN2019/090933 filed on Jun. 12, 2019, which claims the priority of Chinese Patent Application No. 201810608326.0, filed before the CNIPA on Jun. 13, 2018, titled "PREGABALIN SUSTAINED RELEASE COMPOSITION AND METHOD FOR PREPARING THE SAME", and the priority of Chinese Patent Application No. 201811202248.0, filed before the CNIPA on Oct. 16, 2018, titled "PREGABALIN SUSTAINED RELEASE COMPOSITION AND METHOD FOR PREPARING THE SAME", which are incorporated herein by reference in their entirety.

FIELD OF THE INVENTION

The present application relates to the technical field of pregabalin formulation, in particular to a pregabalin sustained release composition and a method for preparing the same.

BACKGROUND OF THE INVENTION

Pregabalin is used to treat neuropathic pain associated with diabetic peripheral neuropathy (DPN) and post-herpetic neuralgia (PHN). Pregabalin as a calcium ion channel modulator inhibits the $\alpha 2$-$\delta$ subunit of the voltage-dependent calcium channel of the central nervous system, which reduce calcium influx, and then reduce the release of excitatory neurotransmitters such as glutamate, norepinephrine, substance P. Pregabalin thereby is effective in controlling neuropathic pain, and has effects of anxiolytics and anticonvulsants.

Clinical studies have shown that the absorption of pregabalin in the gastrointestinal tract is not even. It is well absorbed in the small intestine and ascending colon of humans, but is hardly absorbed in an intestinal segment outside hepatic flexure of colon. This means that the average absorption window of pregabalin is about 6 hours or less. Thus, pregabalin in a conventional sustained release formulation passes through the hepatic flexure of colon after more than 6 hours, and thus the released drug will not be effectively absorbed, resulting in a waste of drugs. Therefore, it has become a technical problem to be solved urgently by those skilled in the art to enhance the absorption of pregabalin in the small intestine and ascending colon.

SUMMARY OF THE INVENTION

The object of examples of the present application is to provide a pregabalin sustained release composition for enhancing the absorption of pregabalin in the small intestine and ascending colon. Meanwhile, the present application also provides a method for preparing pregabalin sustained release composition. The specific technical solutions are as follows.

Firstly provided is a pregabalin sustained release composition comprising:
(a) an active ingredient comprising pregabalin or a pharmaceutically acceptable salt or hydrate thereof;
(b) a matrix-forming agent;
(c) a swelling agent; and
(d) a gelling agent;
wherein the swelling agent comprises one or at least two of crosslinked carmellose sodium, carmellose calcium, sodium carboxymethyl starch, low substituted hydroxypropyl cellulose, and polyoxyethylene.

Pregabalin, with the chemical name (S)-3-aminomethyl-5-methylhexanoic acid, is of the chemical structural formula as follows:

In the present application, pregabalin as an active pharmaceutical ingredient can be prepared by a known method or is commercially available. It can be easily accomplished in either way to obtain by those skilled in the art, which is unnecessary to go into details herein. In some embodiments of the present application, pregabalin is commercially available as an active pharmaceutical ingredient.

In the present application, the pharmaceutically acceptable salt of pregabalin refers to an addition salt with a pharmaceutically acceptable acid or base. Such a pharmaceutically acceptable salt includes, for example, a salt of the acid selected from the group consisting of hydrochloric acid, phosphoric acid, hydrobromic acid, sulfuric acid, sulfurous acid, formic acid, toluenesulfonic acid, methanesulfonic acid, nitric acid, benzoic acid, citric acid, tartaric acid, maleic acid, hydroiodic acid, alkanoic acid (such as acetic acid, HOOC—$(CH_2)_n$—COOH (n is 0-4)) and the like.

Such a pharmaceutically acceptable salt also include, for example, a salt of the base selected from the group consisting of sodium, potassium, calcium, ammonium, and the like. A variety of non-toxic pharmaceutically acceptable addition salts are known to those skilled in the art.

In the present application, a hydrate refers to a molecular complex of a drug (such as pregabalin) and water in a stoichiometric or non-stoichiometric amount.

In some embodiments of the present application, the swelling agent may comprise sodium carboxymethyl starch, and at least one of low substituted hydroxypropyl cellulose and polyoxyethylene. Preferably, the swelling agent comprises sodium carboxymethyl starch and polyoxyethylene.

In further embodiments of the present application, the swelling agent may comprise at least one of carmellose calcium, low substituted hydroxypropyl cellulose and polyoxyethylene. Preferably, the swelling agent comprises polyoxyethylene.

In some embodiments of the present application, the pregabalin or a pharmaceutically acceptable salt or hydrate thereof preferably has a particle size $D_{90}$ ranging from 250 to 600 μm, preferably from 300 to 600 μm, more preferably from 350 to 500 μm.

In some embodiments of the present application, the weight percentage of the active ingredient may be 5%-55%, 5%-50%, 10%-40%, 10%-35%, 20%-30%, or 25%-30%, etc., based on the total weight of the pregabalin sustained release composition.

In some embodiments of the present application, the active ingredient may optionally include at least one additional compound having a synergistic therapeutic effect with pregabalin, in addition to pregabalin or a pharmaceutically acceptable salt or hydrate thereof.

In the present application, use of the matrix-forming agent is to provide structural integrity to the composition, contributes to control or prolong drug release and the like. Those skilled in the art can select a suitable matrix-forming agent in accordance with the description herein for the effect thereof. In some embodiments of the present application, the weight percentage of the matrix-forming agent may be 5%-45%, 5%-40%, 15%-35%, or 15%-30%, etc., based on the total weight of the pregabalin sustained release composition.

In some embodiments of the present application, the matrix-forming agent can be a mixture of polyvinyl acetate and polyvinylpyrrolidone. Polyvinylpyrrolidone (PVP) is a homopolymer of 1-vinylpyrrolidin-2-one generally having a molecular weight Mw of about $1 \times 10^3$ to about $1 \times 10^7$ about $2.5 \times 10^3$ to about $3 \times 10^6$ or about $1 \times 10^4$ to about $1 \times 10^5$. Polyvinylpyrrolidone can be obtained from BASF sold under the trademark of KOLLIDON®, or from ISP sold under the trademark of PLASDONE®. Polyvinyl acetate (PVAc) is a homopolymer of vinyl acetate, and generally has a molecular weight Mw of about $1 \times 10^5$ to about $1 \times 10^6$. The matrix-forming agent may comprise 0% to 90%, 20% to 90%, 60% to 90% or 70% to 85% by weight of PVAc, based on the total weight of PVAc and PVP. In some embodiments of the present application, the matrix-forming agent is a mixture of PVAc and PVP at 80/19 (w/w) available from BASF sold under the trademark of Kollidon® SR (hereinafter referred to as "Kollidon® SR").

In the present application, the swelling agent can absorb water from the gastric juice, thereby resulting in expansion of the pregabalin sustained release composition. It is also possible to control the rate of drug release by, for example, creating a channel or forming a hydrophilic colloid. The swelling agent is soluble or insoluble in water. In some embodiments of the present application, the swelling agent can be 5%-70%, 6.5%-70%, 20%-60%, 9%-50%, 20%-30%, or 9%-29%, etc. by weight based on the total weight of the pregabalin sustained release composition. It is described in the patent application of CN 101330907A that the swelling agent necessarily contains crosslinked polyvinylpyrrolidone (also known as crospovidone). The inventors have unexpectedly found from a large number of experiments that, instead of crosslinked polyvinylpyrrolidone, when one or at least two of crosslinked carmellose sodium, carmellose calcium, sodium carboxymethyl starch, low substituted hydroxypropyl cellulose, and polyoxyethylene are used as a swelling agent, the pregabalin sustained release composition can rapidly swell in volume upon contacting with an aqueous medium, and the volume after swelling is comparable or even better than that described in the above patent. Further, the inventor has also found that the oxide contained in crospovidone has a certain influence on the stability of the composition, and the formulation containing crospovidone is more hygroscopic, which is disadvantageous to the storage thereof.

It should be rioted that the swelling agent used in the present application including croscarmellose sodium, croscarmellose calcium, sodium carboxymethyl starch, low-substituted hydroxypropylcellulose, and polyoxyethylene are all commonly used pharmaceutical adjuvants. Those skilled in the art know their structures, properties and acquiring well and can implement the present application.

In the present application, the gelling agent can alter (e.g., prolong) the drug release characteristics of the composition. The gelling agent includes a synthetic polymer and/or a natural polymer which generally has low water solubility (e.g., slightly soluble to poorly soluble). When contacting with water, the gelling agent form a viscous mixture (with a viscosity greater than water) that prolongs the drug release, such as the time for pregabalin releasing f-om the composition. In some embodiments of the present application, the weight percentage of the gelling agent can be 1%-30%, 1%-20%, 3%-20%, 4%-14%, or 3%-10%, etc., based on the total weight of the pregabalin sustained release composition.

In some embodiments of the present application, the gelling agent is one of carbomer or polysaccharide, or a combination thereof. Preferably, the gelling agent is carbomer, Carbomer is a polymer of acrylic acid bonded to allyl sucrose or pentaerythritol allyl ether. The content of carboxylic acid group (—COOH) is generally from 56.0% to 68.0% in a dry product. The number average molecular weight of carbomer is about $1 \times 10^5$ to about $1 \times 10^{10}$ or about $7 \times 10^5$ to about $4 \times 10^9$.

Polysaccharide is a sugar chain bounded by a glycosidic bond, which is a polymeric carbohydrate composed of more than 10 monosaccharides. In the present application, representative polysaccharides used may include one of xanthan gum, inulin, guar gum, chitosan, locust bean gum or carrageenan, or the combination thereof.

Xanthan gum, also known as corn syrup, is a polysaccharide having a molecular weight Mw of about $2 \times 10^6$. Inulin, also known as oligofructose and polyfructose, is a natural polysaccharide. The number of D-fructose fragments in inulin is generally 2 to about 140, or about 25 to about 30. Guar gum is a hydrophilic colloidal polysaccharide having a molecular weight Mw of about $2 \times 10^5$. Chitosan is a kind of polysaccharide that is poorly soluble in water and composed of a copolymer of β-D-glucosamine and N-acetyl-β-D-glucosamine. The number average molecular weight of chitosan is generally about $1 \times 10^4$ to about $1 \times 10^6$. Locust bean gum is a natural polysaccharide similar to guar gum, and is a galactomannan having a molecular weight Mw of about $5 \times 10^4$ to about $3 \times 10^6$. Carrageenan, commonly known as carrageenin, is a calcium, potassium, sodium, or ammonium salt of polysaccharide sulfate composed of galactose and dehydrated galactose. Due to different binding forms of sulfate, carrageenan can be divided into: κ-type, ι-type, λ-type and the like. Various grades of carrageenan, based on the type of gel, aqueous solubility and viscosity when mixed with water, can be selected. It should be noted that the above polysaccharides are all commercial products, and those skilled in the art can obtain the polysaccharides easily to implement the present application.

In some embodiments of the present application, the pregabalin sustained release composition may further comprise filler. The filler may alter (e.g., prolong) the drug release characteristics of the composition and maintain the rigidity of a drug tablet (luring the drug release process. It is also possible for the filler to alter (e.g., increase) the volume and weight of the pregabalin sustained release composition to facilitate subsequent shaping of the composition, such as tableting and the like. The filler is usually either water-soluble or water-insoluble. The water-soluble filler accelerates dissolution by forming pores in the skeleton after its dissolution. The water-insoluble filler accelerates dissolution by water absorbing and swelling thereof, which leads to infiltration of water into the skeleton. In the present application, filler commonly used in the technical field may be selected, including but not limited to one or at least two of microcrystalline cellulose, lactose, starch, pregelatinized starch, calcium phosphate dihydrate, and anhydrous dicalcium phosphate. In some embodiments of the present application, the weight percentage of the filler may be 1% to 40% based on the total weight of the pregabalin sustained release composition. More specifically, in some embodiments, the weight percentage of the filler may be 1% to 15% or 3% to 8% and the like. In some other embodiments, the weight percentage of the filler is 5% to 40%, preferably 10% to 35%, most preferably 15% to 30% so that the filler can alter (e.g., prolong) the drug release characteristics of the composition more significantly and maintain the rigidity of the drug tablet during the drug release process more effectively.

Further, when the pregabalin sustained release composition comprises both a filler and a swelling agent comprising polyoxyethylene, the pregabalin sustained release composition thus prepared has a greater volume swelling rate. Especially when the filler contains microcrystalline cellulose, the pregabalin sustained release composition thus prepared has a size of 13 mm or more, even 13.5 mm or more 2 hours after contacting with aqueous medium. Meanwhile, the tablet can maintain a good rigidity. This result is very surprising and very useful. It is known to those skilled in the art that the earlier the size is swelled to 13 mm, the more favorable for pregabalin sustained release composition to stay in the stomach, thereby increasing the absorption of pregabalin. The size of the composition increasing to 13 mm in just 2 h is advantageous to maintain pregabalin sustained release composition in the stomach. The good rigidity of tablet prolongs the time for maintaining the tablet shape, ensures sufficient retention time of the composition in the stomach and achieves the sustained release effect. In the present application, the "size" of the composition corresponds to the longest linear dimension of the smallest cross-section of the formulation.

In some examples of the present application, the filler is one or more selected from the group consisting of microcrystalline cellulose, lactose, and pregelatinized starch. Preferably, the filler is microcrystalline cellulose.

In some embodiments of the present application, the pregabalin sustained release composition may further comprise lubricant, which facilitates various processing steps including mixing components, tableting and the like. For example, the lubricant enables a pressure distributed evenly during tableting and uniform density of a tablet, reduced force required to push the tablet out of the die orifice. Another effect of the lubricant may be to improve the appearance of a tablet and to make the surface of a tablet bright and flat. In the present application, lubricants commonly used in the art can be selected, including but not limited to one or a combination of at least two of magnesium stearate, talc powder, micropowder of silica gel, sodium stearyl fumarate, glyceryl behenate and polyethylene glycol, more preferably magnesium stearate. In some embodiments of the present application, the weight percentage of the lubricant can be 0.1%-1.5%, or 0.5%-1%, etc., based on the total weight of the pregabalin sustained release composition.

In some embodiments of the present application, the pregabalin sustained release composition may further comprise coating powder. In the present application, coating powder commonly used in the art may be selected, including but not limited to at least one of polyvinyl alcohol and polyethylene glycol, at least one of silica and talc powder, and/or a flavoring agent. In some embodiments of the present application, the weight percentage of the coating powder may be 2% to 6%, or 3% to 4%, etc., based on the total weight of the pregabalin sustained release composition.

The present application further provides a method for preparing pregabalin sustained release composition described above, comprising:

mixing an active ingredient, a matrix forming agent, a swelling agent and a gelling agent, and optionally filler, and then subjecting the obtained mixture to a shaping process. In a particular implementation, the shaping process can include a process such as granulation, optionally finishing granule, and tableting. In the present application, the sustained release tablet is prepared by a process of direct compression, which is achieved by controlling the particle size $D_{90}$ of active pharmaceutical ingredient of pregabalin to 250-600 µm, preferably 300-600 µm, more preferably 350-500 µm, and selecting a matrix-forming agent, a swelling agent and a gelling agent with good fluidity. In some embodiments, active pharmaceutical ingredient of pregbalin with a different particle size may also be employed, such as pregbalin with $D_{50}$ of 50-200 µm or 50-175 µm. It should be noted that mixing and subsequent shaping are all conventional processes and operations in the art, which are not specifically limited herein.

In addition, in the process of preparing the pregabalin sustained release composition, the inventors investigated the influence of mixing time on content uniformity of the component in the mixture. Unexpectedly, it was found that the longer the mixing time was, the better the content uniformity within 20 minutes can be obtained. After 20 minutes, the content uniformity had no obvious change or even tended to deteriorate. The specific test results are shown in Table 1. On this basis, in some embodiments of the present application, the mixing time in the mixing process is 10-30 min, preferably 10-25 min, more preferably 15 min, and most preferably 20 min. It should be noted that the mixed material referred to herein contains an active ingredient, a matrix-forming agent, a swelling agent, a gelling agent, and optionally filler.

TABLE 1

| Mixing time (min) | 5 | 10 | 15 | 20 | 25 | 30 |
|---|---|---|---|---|---|---|
| Content uniformity of the component in the mixture RSD (%) | 6.5 | 3.0 | 1.3 | 1.2 | 1.3 | 1.6 |

In some embodiments of the present application, when lubricant is contained in the pregabalin sustained release composition, the active ingredient, the matrix-forming agent, the swelling agent, the gelling agent, and optionally the filler may be mixed, and then A: mixed with all lubricant, and then subjected to the shaping process;

or

B: mixed with a part of the lubricant, subjected to granulating, optionally finishing granule, added with remaining lubricant, and then subjected to another step of the shaping process, such as tableting.

In some embodiments of the present application, when coating powder is contained in the pregabalin sustained release composition, the method further comprises a coating process by using a film coating premix after the shaping process. The film coating premix may comprise at least one of polyvinyl alcohol and polyethylene glycol, at least one of silica and talc powder, and/or a flavoring agent. The solid content of the film coating premix may be 10% to 25%. Further, the solid content of the film coating premix may be from 10% to 15%. It should be noted that the coating process is also conventional processes and operations in the art, which is not specifically limited herein.

The pregabalin sustained release composition provided herein can be in the form of a tablet. On this basis, the present application also provides a pregabalin sustained release tablet comprising the pregabalin sustained release composition aforementioned.

The pregabalin sustained release composition provided in present application can rapidly swell when exposed to an aqueous medium, and exceed the diameter of human gastric pylorus (13 mm). It thus can prolong the gastric emptying time to increase the retention time of pregabalin in the stomach and improve the absorption of pregabalin in the small intestine and ascending colon. At the same time, the pregabalin sustained release composition provided in the present application achieves a sustained release for 24 h, which allows QD (once a day) administration, reduces administration times, and improves the patient compliance.

DESCRIPTION OF THE DRAWINGS

In order to illustrate the embodiments of the examples of the present application and the prior art more clearly, the drawings used in the following description of the embodiments and the prior art will be briefly described. It is obvious to those skilled in the art that the accompanying drawings in the following description are only some examples of the application, and other drawings can be obtained from these drawings without any inventive efforts.

DETAILED DESCRIPTION OF THE INVENTION

In order to make the technical problems, technical solutions and effects of the present application more clear, the present application will be further described in conjunction with specific examples as follows. In the following examples, the specific conditions of the experiment methods described are generally carried out under conventional conditions or conditions recommended by the manufacturer, unless otherwise stated. The starting materials and reagents are all commercially available or prepared according to published information.

Preparation Example of a Pregabalin Sustained Release Tablet (an Oval Tablet)

The English abbreviations used in the following examples are shown in Table 2 below.

TABLE 2

| | |
|---|---|
| Kollidon ® SR | A mixture of polyvinyl acetate and polyvinyl-pyrrolidone |
| PVPP | Crospovidone |
| PEO | Polyoxyethylene |
| MCC | Microcrystalline cellulose |
| CMS-Na | Sodium carboxymethyl starch |
| CC-Na | Crosslinked carmellose sodium |
| L-HPC | Low substituted hydroxypropyl cellulose |

Example 1

Formulation:

| Drug/adjuvant | Dosage (g) |
|---|---|
| Pregbalin | 330 |
| Kollidon ® SR | 256.5 |
| CMS-Na | 150 |
| PEO | 313.3 |
| Carbomer 974P | 69.6 |
| Magnesium stearate | 5.6 |
| Produced into | 1125 g/1000 tablets |

Preparation method: according to the formulation dosage, pregabalin, Kollidon® SR, CMS-Na and carbomer 974P was weighed and passed through a 40 mesh sieve together, added with PEO and mixed for 15 mi in a mixer, added with magnesium stearate and mixed for 5 min, and tableted.

Example 2

Formulation:

| Drug/adjuvant | Dosage (g) |
|---|---|
| Pregbalin | 330 |
| Kollidon ® SR | 169 |
| PEO | 313 |
| Carbomer 974P | 308 |
| Magnesium sterate | 5.6 |
| Produced into | 1125 g/1000 tablets |

Preparation method: according to the formulation dosage, pregabalin, Kollidon® SR and Carbomer 974P was weighed and passed through a 40 mesh sieve together, added with PEO and mixed for 10 min in a mixer, added with magnesium stearate in half of the formulation dosage and mixed for 5 min. The mixture was subjected to dry granulating, finishing granule by passing through a 20 mesh sieve, then added with the remaining half magnesium stearate, mixed for 10 min and tableted.

Example 3

Formulation:

| Drug/adjuvant | Dosage (g) |
|---|---|
| Pregbalin | 330 |
| Kollidon ® SR | 257 |
| CMS-Na | 225 |
| PEO | 239 |
| Carbomer 974P | 70 |
| Magnesium stearate | 5.6 |
| Produced into | 1125 g/1000 tablets |

Preparation method: according to the formulation dosages, pregabalin, Kollidon® SR, CMS-Na and Carbomer 974P was weighed and passed through a 40 mesh sieve together, added with PEO and mixed for 15 min in a mixer, then added with magnesium stearate and mixed for 5 min, and tableted.

Example 4

Formulation:

| Drugs/adjuvant | Dosage (g) |
| --- | --- |
| Pregbalin | 330 |
| Kollidon ® SR | 169 |
| CMS-Na | 225 |
| PEO | 326 |
| Carbomer 974P | 70 |
| Magnesium stearate | 5.6 |
| Produced into | 1125 g/1000 tablets |

Preparation method: according to the formulation dosage, pregabalin, Kollidon® SR. CMS-Na and Carbomer 974P was weighed and passed together through a 40 mesh sieve, added with PEO and mixed for 15 min in a mixer, then added with magnesium stearate and mixed for 5 min, and tableted.

Example 5

Formulation:

| Drug/adjuvant | Dosage (g) |
| --- | --- |
| Pregbalin | 330 |
| Kollidon ® SR | 257 |
| CC-Na | 225 |
| PEO | 239 |
| Carbomer 974P | 70 |
| Magnesium stearate | 5.6 |
| Produced into | 1125 g/1000 tablets |

Preparation method: according to the formulation dosage, pregabalin, Kollidon® SR, CC—Na and carbomer 974P was weighed and passed together through a 40 mesh sieve, added with PEO, mixed for 15 m in in a mixer, then added with magnesium stearate, mixed for 5 min, and tableted.

Example 6

Formulation:

| Drug/adjuvant | Dosage (g) |
| --- | --- |
| Pregbalin | 330 |
| Kollidon ® SR | 257 |
| L-HPC | 225 |
| PEO | 239 |
| Carbomer 974P | 70 |
| Magnesium sterate | 5.6 |
| Produced into | 1125 g/1000 tablets |

Preparation method: according to the formulation dosage, pregabalin, Kollidon® SR, L-HPC and Carbomer 974P was weighed and passed together through a 40 mesh sieve, added with PEO, mixed for 15 min in a mixer, then added with magnesium stearate, mixed for 5 ruin, and tableted.

Example 7

Formulation:

| Drug/adjuvant | Dsssge (g) |
| --- | --- |
| Pregbalin | 330 |
| Kollidon ® SR | 257 |
| L-HPC | 225 |
| PEO | 239 |
| Chitosan | 70 |
| Magnesium stearate | 5.6 |
| Produced into | 1125 g/1000 tablets |

Preparation method: according to the formulation dosage, pregabalin, Kollidon® SR, L-HPC and chitosan was weighed and passed together through a 40 mesh sieve, added with PEO, mixed for 15 min in a mixer, then added with magnesium stearate, mixed for 5 min, and tableted.

Example 8

Formulation:

| Drug/adjuvant | Dosage (g) |
| --- | --- |
| Pregbalin | 330 |
| Kollidon ® SR | 257 |
| CMS-Na | 225 |
| PEO | 239 |
| Carbomer 974P | 70 |
| Magnesium stearate | 5.6 |
| Film coating premix | 35 |
| Produced into | 1160 g/1000 tablets |

Preparation method: according to the formulation dosage, pregabalin, Kollidon® SR, CMS-Na and Carbomer 974P was weighed and passed together through a 40 mesh sieve, added with PEO and mixed for 15 win in a mixer, then added with magnesium stearate and mixed for 5 min, tableted. The tablet was coated with a film coating premix of 12% (w/w) solid content, with an increased weight up to 3% by coating. The film coating premix contained polyvinyl alcohol, silica, tale powder, polyethylene glycol and a flavoring agent, and it was obtained by dissolving the above materials in purified water and passing through an 80 mesh sieve.

Example 9

Formulation:

| Drug/adjuvant | Dosage (g) |
| --- | --- |
| Pregbalin | 330 |
| Kollidon ® SR | 300 |
| PEO | 295 |
| Carbomer 974P | 115 |
| Microcrystalline cellulose | 80 |
| Magnesium stearate | 5 |
| Produced into | 1125 g/1000 tablets |

Preparation method: according to the formulation dosage, pregabalin, Kollidon® SR, microcrystalline cellulose and Carbomer 974P was weighed and passed together through a 40 mesh sieve, added with PEO and mixed for 15 min in a mixer, then added with magnesium stearate and mixed for 5 ruin, and tableted.

Example 10

Formulation:

| Drug/adjuvant | Dosage (g) |
|---|---|
| Pregbalin | 330 |
| Kollidon ® SR | 250 |
| CMS-Na | 225 |
| PEO | 245 |
| Carbomer | 69 |
| Magnesium stearate | 6 |
| Produced into | 1125 g/1000 tablets |

Preparation method: according to the formulation dosage, pregabalin, Kollidon® SR, CMS-Na and Carbomer was weighed and passed together through an 18 mesh sieve, added with PEO and mixed for 15 min in a mixer, then added with magnesium stearate and mixed for 5 min, and tableted.

Example 11

Formulation:

| Drug/adjuvant | Dosage (g) |
|---|---|
| Pregbalin | 330 |
| Kollidon ® SR | 250 |
| Carmellose calcium | 225 |
| PEO | 245 |
| Carbomer | 69 |
| Magnesium stearate | 6 |
| Produced into | 1125 g/1000 tablets |

Preparation method: according to the formulation dosage, prepremarin, Kollidon® SR, carmellose calcium and Carbomer was weighed and passed together through a 18 mesh sieve, added with PEO and mixed for 10 min in a mixer, then added with magnesium stearate in half of the formulation dosage and mixed for 5 min. The mixture was subjected to dry granulating, finishing granule by passing through a 20 mesh sieve, then added with the remaining half magnesium stearate, mixed for 10 min and tableted.

Example 12

Formulation:

| Drug/adjuvant | Dosage (g) |
|---|---|
| Pregbalin | 330 |
| Kollidon ® SR | 250 |
| L-HPC | 225 |
| PEO | 245 |
| Carbomer | 69 |
| Magnesium stearate | 6 |
| Produced into | 1125 g/1000 tablets |

Preparation method: according to the formulation dosage, pregabalin, Kollidon® SR, L-HPC and Carbomer was weighed and passed together through an 18 mesh sieve, added with PEO and mixed for 15 min in a mixer, then added with magnesium stearate and mixed for 5 min, and tableted.

Example 13

Formulation:

| Drug/adjuvant | Dosage (g) |
|---|---|
| Pregbalin | 330 |
| Kollidon ® SR | 250 |
| Microcrystalline cellulose | 225 |
| PEO | 245 |
| Carbomer | 69 |
| Magnesium stearate | 6 |
| Produced into | 1125 g/1000 tablets |

Preparation method: according to the formulation dosage, pregabalin, Kollidon® SR, microcrystalline cellulose and carbomer was weighed and passed together through an 18 mesh sieve, added with PEO and mixed for 15 min in a mixer, then added with magnesium stearate and mixed for 5 min, and tableted.

Example 14

Formulation:

| Drug/adjuvant | Dosage (g) |
|---|---|
| Pregbalin | 330 |
| Kollidon ® SR | 250 |
| CC-Na | 225 |
| PEO | 245 |
| Carbomer | 69 |
| Magnesium stearate | 6 |
| Produced into | 1125 g/1000 tablets |

Preparation method: according to the formulation dosage, pregabalin, Kollidon® SR, CC—Na and Carbomer was weighed and passed together through a 18 mesh sieve, added with PEO and mixed for 15 min in a mixer, then added with magnesium stearate and mixed for 5 min, and tableted.

Example 15

Formulation:

| Drug/adjuvant | Dosage (g) |
|---|---|
| Pregbalin | 330 |
| Kollidon ® SR | 270 |
| Pregelatinized starch | 227 |
| PEO | 180 |
| Carbomer | 113 |
| Magnesium stearate | 6 |
| Produced into | 1125 g/1000 tablets |

Preparation method: according to the formulation dosage, pregabalin, Kollidon® SR, pregelatinized starch and Carbomer was weighed and passed together through an 18 mesh sieve, added with PEO and mixed for 20 min in a mixer then added with magnesium stearate and mixed for 5 min, and tableted.

Example 16

Formulation:

| Drug/adjuvant | Dosage (g) |
|---|---|
| Pregabalin | 330 |
| Kollidon ® SR | 281 |
| Microcrystalline cellulose | 169 |
| PEO | 284 |
| Carbomer | 56 |
| Magnesium stearate | 6 |
| Produced into | 1125 g/1000 tablets |

Preparation method: according to the formulation dosage, pregabalin, Kollidon® SR, microcrystalline cellulose and Carbomer was weighed and passed together through an 18 mesh sieve, added with PEO and mixed for 15 min in a mixer, then added with magnesium stearate and mixed for 5 win, and tableted.

Example 17

Formulation:

| Drug/adjuvant | Dosage (g) |
|---|---|
| Pregbalin | 330 |
| Kollidon ® SR | 281 |
| Microcrystalline cellulose | 169 |
| PEO | 284 |
| Carbomer | 56 |
| Magnesium stearate | 6 |
| Film coating premix | 35 |
| Produced into | 1160 g/1000 tablets |

Preparation method: according to the formulation dosage, pregabalin, Kollidon® SR, microcrystalline cellulose and Carbomer was weighed and passed together through an 18 mesh sieve, added with PEO and mixed for 20 min in a mixer, then added with magnesium stearate and mixed for 5 min, and tableted. The tablet was coating with a film coating premix of 20% (w/w) solid content, with an increased weight of 3% by coating. The film coating premix contained polyvinyl alcohol, silica, talc powder, polyethylene glycol and a flavoring agent, and it was obtained by dissolving the above materials in purified water and passing through an 80 mesh sieve.

Example 18-26

Examples 18-26 were performed with reference to the preparation method of Example 8 and the formulation in Table 3 below.

TABLE 3

| | Example | | | | | | | | |
|---|---|---|---|---|---|---|---|---|---|
| Ingredient name | 18 Proportion in the formulation (%) | 19 Proportion in the formulation (%) | 20 Proportion in the formulation (%) | 21 Proportion in the formulation (%) | 22 Proportion in the formulation (%) | 23 Proportion in the formulation (%) | 24 Proportion in the formulation (%) | 25 Proportion in the formulation (%) | 26 Proportion in the formulation (%) |
| Pregabalin | 5 | 10 | 15 | 20 | 35 | 40 | 25 | 30 | 55 |
| Kollidon ® SR | 30 | 10 | 15 | 25 | 5 | 35 | 40 | 40 | 35 |
| CMS-Na | 0 | 0 | 20 | 0 | 0 | 0 | 5 | 5 | 5 |
| CC-Na | 0 | 0 | 0 | 40 | 40 | 10 | 0 | 0 | 0 |
| L-HPC | 0 | 0 | 0 | 0 | 0 | 0 | 0 | 0 | 0 |
| PEO | 60 | 70 | 34 | 0 | 0 | 0 | 0 | 0 | 0 |
| Carbomer 974P | 2 | 5 | 5 | 10 | 10 | 5 | 20 | 3 | 3 |
| Chitosan | 0 | 0 | 0 | 0 | 0 | 0 | 0 | 0 | 0 |
| Microcrystalline cellulose | 3 | 3 | 8 | 0 | 0 | 0 | 0 | 0 | 0 |
| Magnesium stearate | 1 | 0.5 | 1.5 | 1 | 10 | 7 | 7 | 0.5 | 0.5 |
| Film coating premix | 0 | 2.5 | 1.5 | 4 | 0 | 3 | 3 | 1.5 | 1.5 |
| Tablet weight | 1000 | 1000 | 1125 | 1125 | 1125 | 1125 | 1125 | 1125 | 1125 |

Example 27-34

Examples 27-34 were performed with reference to the preparation method of Example 17 and the formulation in Table 4 below.

Preparation method: according to the formulation dosage, pregabalin and PEO was weighed, mixed for 15 min in a mixer, then added with magnesium stearate, mixed for 5 min, and tableted.

TABLE 4

| Ingredient name | Example 27 Proportion in the formulation (%) | 28 Proportion in the formulation (%) | 29 Proportion in the formulation (%) | 30 Proportion in the formulation (%) | 31 Proportion in the formulation (%) | 32 Proportion in the formulation (%) | 33 Proportion in the formulation (%) | 34 Proportion in the formulation (%) |
|---|---|---|---|---|---|---|---|---|
| Pregabalin | 5 | 10 | 10 | 20 | 35 | 30 | 25 | 50 |
| Kollidon ® SR | 30 | 12.5 | 15 | 25 | 5 | 35 | 40 | 40 |
| CMS-Na | 0 | 0 | 10 | 0 | 0 | 0 | 0 | 0 |
| Carmellose calcium | 0 | 0 | 0 | 40 | 0 | 0 | 10 | 0 |
| Microcrystalline cellulose | 35 | 0 | 40 | 0 | 30 | 0 | 10 | 0 |
| Pregelatinized starch | 0 | 0 | 0 | 0 | 0 | 5 | 0 | 0 |
| PEO | 25 | 70 | 19 | 0 | 9 | 25 | 5 | 6.5 |
| Carbomer | 4 | 7 | 5 | 14 | 20 | 4.5 | 9.5 | 3 |
| Magnesium stearate | 1 | 0.5 | 1 | 1 | 1 | 0.5 | 0.5 | 0.5 |
| Film coating premix | 0 | 2.5 | 1.5 | 4 | 2 | 3 | 3 | 1.5 |
|  | 100 | 100 | 100 | 100 | 100 | 100 | 100 | 100 |

Comparative Example 1

Refer to Example 30 in CN101330907A.

Comparative Example 2

Formulation:

| Drug/adjuvant | Dosage (g) |
|---|---|
| Pregbalin | 330 |
| Kollidon ® SR | 257 |
| PEO | 533 |
| Magnesium stearate | 5.6 |
| Produced into | 1125 g/1000 tablets |

Preparation method: according to the formulation dosage, pregbalin and Kollidon® SR was weighed and passed together through a 40 mesh sieve, added with PEO and mixed for 15 min in a mixer, then added with magnesium stearate and mixed for 5 min, and tableted.

Comparative Example 3

Formulation:

| Drug/adjuvant | Dosage (g) |
|---|---|
| Pregbalin | 330 |
| PEO | 790 |
| Magnesium stearate | 5.6 |
| Produced into | 1125 g/1000 tablets |

Comparative Example 4

Formulation:

| Drug/adjuvant | Dosage (g) |
|---|---|
| Pregbalin | 330 |
| Kollidon ® SR | 257 |
| Carbomer 974P | 533 |
| Magnesium stearate | 5.6 |
| Produced into | 1125 g/1000 tablets |

Preparation method: according to the formulation dosage, prepremarin, Kollidon® SR and Carbomer 974P was weighed and passed together through a 40 mesh sieve, mixed for 10 min in a mixer, then added with magnesium stearate in half of the formulation dosage and mixed for 5 min. The mixture was subjected to dry granulating, finishing granule by passing through a 20 mesh sieve, then added with the remaining magnesium stearate, mixed for 10 min and tableted.

Drug Dissolution and Swelling Test

Test I

Dissolution test of the tablets of Examples 1-8 and Comparative Example 1

1. Dissolution Method:
   1) Method: Dissolution assay (Chinese Pharmacopoeia, 2015, Vol. IV, General Rules "0931 Dissolution And Release Assay" The Second Method (Paddle Method), with a sinker);
   2) Dissolution medium: 0.06 mol/L HCL, 900 ml;
   3) Rotate Speed: 50 rpm;
   4) Sampling time: 1 h, 2 h, 4 h, 6 h, 9 h, 12 h, 16 h, and 24 h;
   5) Detection method: high performance liquid phase chromatography, with a detection wavelength of 210 nm;

6) Preparation of tested solution: 10 ml of the solution was taken at each time point and filtered;
7) Preparation of the control solution: pregabalin control sample was prepared into a control solution with a concentration of about 360 μg/ml in 0.06 mol/L HCl.

2. Instrument Model:

Smart Dissolution Tester (Model: DT820, Manufacturer: Erweka, Ltd., Germany)

3. Dissolution Results

Figure 1:
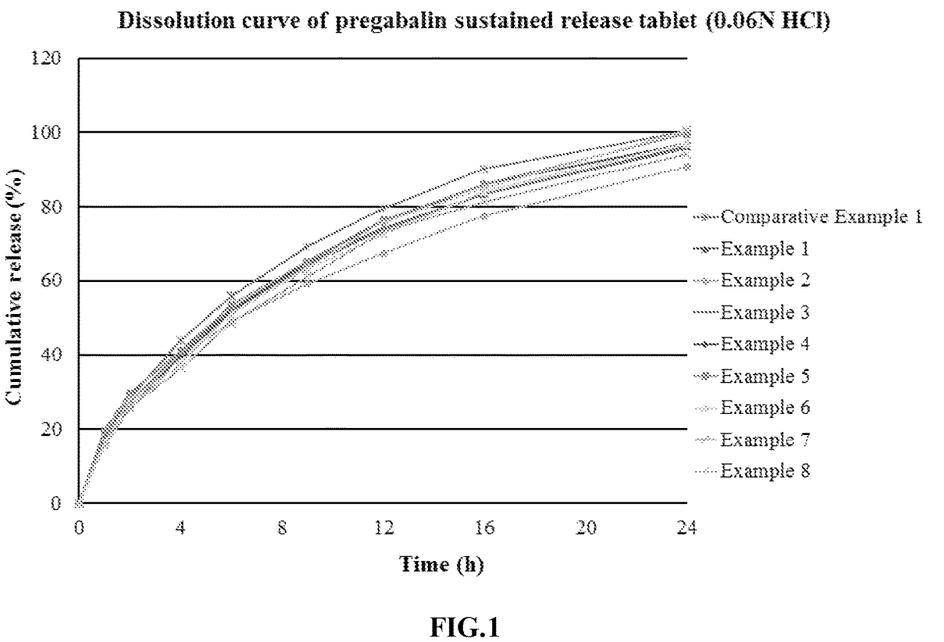
FIG. 1 is a dissolution profile of Examples 1-8 and Comparative Example 1 of the present application.

The dissolution results of Examples 1-8 and Comparative Example 1 in 0.06 mol/L HCl medium are shown in Table 5 and FIG. 1:

Test II

Test for Swelling Size of the Tablets of Examples 1-8 and Comparative Examples 14:

The tablets prepared in the above examples were subjected to a dissolution test according to Chinese Pharmacopoeia, 2015, Vol. IV, General Rules "0931 Dissolution And Release Assay", The Second Method (Paddle Method). 900 nil 0.06 N HCl solution was used as a dissolution medium at a rotation speed of 50 rpm. The drug was collected from the dissolution medium at 1 h, 2 h, and 6 h of the dissolution test.

The size was measured with an electronic vernier caliper, and compared with the size of the tablet at 0 h (the tablet before test). The results are shown in Table 6 below:

TABLE 6

| Sample | Length * Width * Thickness | | | |
|---|---|---|---|---|
| | 0 h | 1 h | 2 h | 6 h |
| Example 1 | 20.7 × 10.1 × 7.3 | 22.7 × 12.9 × 9.7 | 24.3 × 14.2 × 13.6 | 25.7 × 15.2 × 14.8 |
| Example 2 | 20.7 × 10.1 × 9.2 | 22.1 × 12.1 × 11.2 | 23.1 × 13.2 × 12.2 | 25.7 × 14.8 × 13.9 |
| Example 3 | 20.6 × 10.1 × 7.9 | 23.6 × 13.5 × 12.1 | 25.2 × 14.2 × 13.3 | 27.2 × 15.8 × 14.9 |
| Example 4 | 20.6 × 10.1 × 7.4 | 23.8 × 14.2 × 12.9 | 25.4 × 14.7 × 13.7 | 27.4 × 15.9 × 15.2 |
| Example 5 | 20.7 × 10.1 × 8.6 | 22.7 × 12.9 × 10.6 | 24.9 × 14.1 × 12.1 | 27.7 × 15.7 × 14.8 |
| Example 6 | 20.7 × 10.1 × 9.1 | 22.1 × 12.1 × 11.1 | 24.7 × 13.8 × 12.9 | 27.5 × 15.1 × 14.9 |
| Example 7 | 20.6 × 10.1 × 8.7 | 22.6 × 12.4 × 10.7 | 25.9 × 13.5 × 13.0 | 28.9 × 14.5 × 13.7 |
| Example 8 | 20.7 × 10.1 × 8.3 | 23.7 × 13.1 × 12.3 | 25.3 × 14.0 × 13.1 | 27.3 × 14.9 × 14.6 |
| Comparative Example 1 | 17.1 × 17.7 × 6.7 | 18.2 × 19.3 × 9.5 | 19.8 × 20.1 × 11.4 | 23.8 × 22.1 × 13.4 |
| Comparative Example 2 | 20.6 × 10.1 × 7.5 | 23.6 × 13.4 × 10.5 | 25.2 × 16.1 × 11.5 | 27.2 × 18.1 × 8.5 |
| Comparative Example 3 | 20.6 × 10.1 × 7.4 | 22.1 × 12.4 × 8.3 | — | — |
| Comparative Example 4 | 20.7 × 10.1 × 9.1 | 24.8 × 12.1 × 10.8 | 27.1 × 13.0 × 11.4 | 31.9 × 14.5 × 12.6 |

Note:

For the Comparative Example 2, the swelled sample first became larger, and then as the swelling continued, the tablet became soft with poor mechanical strength and low thickness of the tablet, which collapsed on the test table after taking out. The sample of Comparative Example 3 was deformed after swelling for 6 h, so that the length, width and thickness of the tablet cannot be measured.

TABLE 5

| | Batch number | | | | | | | | |
|---|---|---|---|---|---|---|---|---|---|
| | 1 h | 2 h | 4 h | 6 h | 9 h | 12 h | 16 h | 24 h | $f_2$ |
| Comparative Example 1 | 18.4 | 28.6 | 44.0 | 55.8 | 69.1 | 79.6 | 90.2 | 100.4 | NA |
| Example 1 | 17.3 | 27.1 | 41.3 | 52.4 | 64.8 | 74.3 | 83.5 | 96.5 | 69 |
| Example 2 | 18.0 | 27.2 | 39.7 | 48.9 | 59.2 | 67.4 | 77.5 | 90.9 | 54 |
| Example 3 | 17.8 | 27.1 | 40.9 | 51.7 | 64.1 | 73.7 | 83.4 | 95.8 | 67 |
| Example 4 | 16.2 | 25.7 | 39.8 | 51.4 | 65.1 | 75.7 | 86.4 | 97.1 | 69 |
| Example 5 | 19.8 | 29.8 | 41.1 | 53.1 | 65.2 | 76.4 | 86 | 99.7 | 74 |
| Example 6 | 15.7 | 25.8 | 38.1 | 51.0 | 63.1 | 72.4 | 84.1 | 97.1 | 64 |
| Example 7 | 15.9 | 25.8 | 36.5 | 48.5 | 61.1 | 73.1 | 81.4 | 94.2 | 58 |
| Example 8 | 16.4 | 28.1 | 37.4 | 51.2 | 63.4 | 75.7 | 85.1 | 100.7 | 65 |

Note:

All of the dissolution results in the table we expressed in percentage.

As can be seen from Table 5 and FIG. 1, the pregabalin sustained release tablets prepared in Examples 1-8 of the present application were sustained released over 24 h, with a release amount of <30% at 2 h and 60% to 80% at 12 h. A complete release can be observed at 24 h. The dissolution characteristics are substantially the same as those of the sustained release tablets (Comparative Example 1) described in CN 101330907A, thus QD administration can be achieved.

As can be seen from Table 6, the tablets prepared in Examples 1, 3, 4, and 8 of the present application had a size of more than 13 mm after 2 h swelling (this size corresponds to the longest linear dimension of the smallest cross section of the formulation), which was obviously superior to that of Comparative Example 1. In other examples, the swelling size also reached 13 mm or more after 6 h. This size can effectively prolong the retention time of the sustained release tablet in the stomach by mechanical retardation. The pharmaceutical composition can continuously release pregabalin in the stomach, resulting in a much wider absorption window of pregabalin and enhanced absorption thereof in the small intestine and ascending colon. QD administration of the pharmaceutical composition can be achieved. Further, in comparison with Comparative Examples 2-4 without at least one of the matrix-forming agent, the swelling agent, and the gelling agent, the swelling size is greater in Examples 1-8.

Test III

Dissolution test of Examples 10-17 and a control formulation (Lyrica® CR)

The dissolution method can be referred to test I. The sampling time was 1 h, 2 h, 4 h, 6 h, 8 h, 10 h, 12 h, 16 h, and 24 h. The smart dissolution tester was the same as that in test I.

Figure 2:
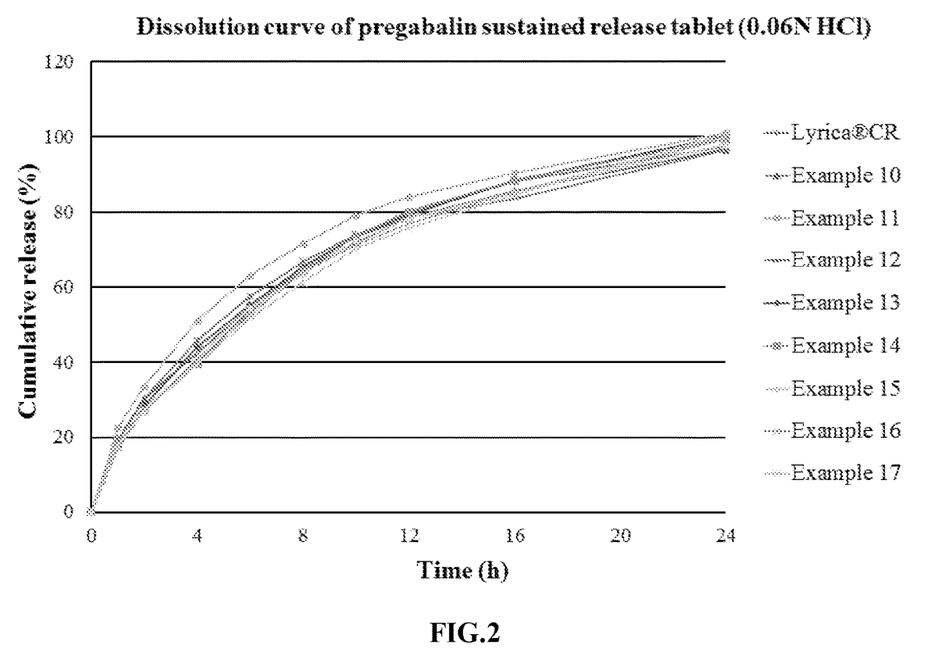
FIG. 2 is a dissolution profile of Examples 10-17 of the present application and the control pregabalin formulation sold under the trademark Lyrica® CR (hereinafter referred to as "Lyrica® CR")

The dissolution results of Examples 10-17 and control formulation (Lyrica® CR) with 0.06 mol/L HCl medium are shown in Table 7 and FIG. 2:

TABLE 7

| Batch number | 1 h | 2 h | 4 h | 6 h | 8 h | 10 h | 12 h | 16 h | 24 h | f₂ |
|---|---|---|---|---|---|---|---|---|---|---|
| Lyrica ® CR | 18.8 | 30.0 | 45.7 | 57.5 | 66.7 | 74.0 | 79.7 | 88.2 | 97.4 | NA |
| Example 10 | 19.5 | 30.1 | 42.4 | 54.4 | 64.2 | 71.9 | 78.4 | 85.6 | 96.7 | 81 |
| Example 11 | 22.5 | 33.5 | 51.1 | 63.0 | 71.5 | 79.2 | 84.1 | 90.5 | 101.1 | 67 |
| Example 12 | 17.1 | 27.1 | 39.5 | 53.3 | 65.2 | 73.4 | 78.5 | 83.5 | 96.5 | 72 |
| Example 13 | 17.5 | 28.1 | 44.1 | 55.3 | 65.3 | 73.4 | 79.2 | 88.4 | 100.2 | 88 |
| Example 14 | 17.6 | 27.2 | 39.7 | 53.9 | 64.4 | 73.5 | 80.2 | 88.4 | 99.5 | 76 |
| Example 15 | 17.8 | 26.8 | 41.6 | 54.5 | 63.4 | 72.5 | 78.3 | 85.3 | 98.1 | 77 |
| Example 16 | 19.8 | 27.2 | 40.8 | 52.6 | 64.1 | 71.2 | 77.1 | 85.3 | 99.6 | 73 |
| Example 17 | 17.8 | 27.1 | 39.5 | 51.7 | 61.2 | 70.1 | 75.7 | 84.5 | 100.8 | 67 |

Note:
All of the dissolution results in the table we expressed in percentage.

As can be seen from Table 7 and FIG. 2, the pregabalin sustained release tablets prepared in Examples 10-17 of the present application were slowly released over 24 h, with a release amount of <25% at 1 h and above 60% at 8 h. Nearly 100% release can be observed at 24 h. The dissolution characteristics are substantially the same as those of the sustained release tablets in Comparative Example 1 and Lyrica® CR, thus QD administration can be achieved.

Test IV

Test for Swelling Size of the Tablets of Examples 10-17 and Lyrica® CR:

The test method can be referred to Test IL. The results are shown in Table 8 below:

TABLE 8

| | Length * Width * Thickness | | | |
|---|---|---|---|---|
| Sample | 0 h | 1 h | 2 h | 6 h |
| Lyrica ®CR | 22.3 × 11.0 × 6.9 | 24.3 × 13.0 × 7.1 | 24.4 × 13.2 × 9.7 | 26.5 × 13.8 × 10.6 |
| Example 10 | 20.7 × 10.1 × 7.8 | 22.7 × 12.9 × 9.1 | 24.3 × 14.2 × 12.6 | 25.7 × 15.2 × 13.1 |
| Example 11 | 20.7 × 10.1 × 7.8 | / | / | / |
| Example 12 | 20.7 × 10.1 × 7.9 | 23.5 × 13.5 × 11.2 | 24.1 × 14.3 × 12.5 | 27.2 × 15.8 × 13.9 |
| Example 13 | 20.7 × 10.1 × 7.4 | 23.4 × 14.2 × 11.5 | 25.1 × 14.7 × 12.7 | 27.4 × 15.9 × 14.1 |
| Example 14 | 20.7 × 10.1 × 7.8 | 22.4 × 12.9 × 11.4 | 24.4 × 14.1 × 12.5 | 27.7 × 15.7 × 14.1 |
| Example 15 | 20.7 × 10.1 × 8.8 | 22.1 × 12.1 × 11.5 | 24.7 × 13.8 × 13.0 | 27.5 × 15.1 × 14.6 |
| Example 16 | 20.7 × 10.1 × 8.3 | 22.5 × 12.4 × 11.3 | 25.4 × 13.5 × 12.5 | 28.1 × 14.5 × 13.7 |
| Example 17 | 20.7 × 10.1 × 8.3 | 23.7 × 13.1 × 11.4 | 25.3 × 14.0 × 12.6 | 27.3 × 14.9 × 13.6 |

Note:
After the sample of Example 11 was dissolved for 1 h, the sample was dispersed, and the size could not be measured.

As can be seen from Table 8, the tablets prepared in the examples of the present application have a size of 13 mm or more after swelling for 2 h (this size corresponds to the longest linear dimension of the smallest cross section of the formulation), similar to the Lyrica® CR (in this study, the difference in initial tablet size was due to the difference in tablet form). The increase in thickness of the tablet was greater than that in the comparative example and Lyrica® CR tablets. This size can effectively prolong the retention time of the sustained release tablet in the stomach by mechanical retardation. The pharmaceutical composition can continuously release pregabalin in the stomach, resulting in a much wider absorption window of pregabalin, and enhanced absorption thereof in the small intestine and ascending colon. QD administration of the pharmaceutical composition can be achieved.

Drug Rigidity Assay

Dissolution test of tablets of Examples 1_0-16 and Lyrica® CR

1. Test Method:

The tablets prepared in Examples 10 to 16 were subjected to a dissolution test with a sinker, according to Chinese Pharmacopoeia, 2015, Vol IV General Rules "0931 Dissolution And Release Assay", The Second Method (Paddle Method). 900 ml of 0.06 mol/L HCl solution was used as the dissolution medium, and the dissolution test was carried out at 37±5° C. at a paddle speed of 50 rpm. The drug was collected from the medium at 2 h, 6 h and 24 h after the test started. The sample rigidity was measured under the following predetermined conditions. The test results are shown in Table 9.

Instrument: Texture Tester (EZ Test)

Load unit: 5 kg

Probe: ¼ sphere probe

Trigger force: 0.5 g

Test speed: 0.2 m/s

Acquisition rate: 10 samples/s

Test distance: 8-10 mm

TABLE 9

| Time (h) | Example 10 | Example 11 | Example 12 | Example 13 | Example 14 | Example 15 | Example 16 | Lyrica® CR |
|---|---|---|---|---|---|---|---|---|
| 2 | 3580 | 3802 | 3750 | 4480 | 3211 | 4108 | 4753 | 4450 |
| 6 | 850 | 1250 | 1009 | 1912 | 998 | 1909 | 1981 | 1760 |
| 24 | 485 | 635 | 601 | 708 | 604 | 681 | 698 | 800 |

As can be seen from Table 9, the tablets prepared in Examples 10, 11, 12 and Example 14 of the present application were less rigid than the tablets of Lyrica® CR after 2 h, 6 h and 24 h. The tablets containing a filler in Examples 13, 15 and 16 were significantly more rigid and significantly superior than the tablets of Lyrica® CR. The rigidity of the tablets during dissolution can protect the tablets from being destroyed by food in the gastrointestinal tract, thereby prolonging the retention time of the tablets in the stomach to widen the absorption window. The absorption of pregabalin in the small intestine and ascending colon is increased to allow QD administration. From the results of the measurement, the use of filler in the present application are effective in increasing the rigidity of the formulation, maintaining the shape of the drug, and ensuring sustained release of the drug.

Drug Stability Test

The influencing factors of Example 17 and the control formulation Lyrica® CR were investigated. The appearance traits, weight gain or loss, dissolution, Content and related substances of the samples in 30 days are shown in Table 10 to Table 14.

TABLE 10

Results of appearance traits

| Sample | Test condition | Trait 0 d | Time 5 d | 10 d | 30 d |
|---|---|---|---|---|---|
| Lyrica ®CR | High temperature test (° C.): 60 ± 2 | Pink film-coated tablets, white after removal of the coating | — | Same as 0 d | Same as 0 d |
| | High temperature test (° C.): 40 ± 2 | Pink film-coated tablets, white after removal of the coating | — | Same as 0 d | Same as 0 d |
| | Intense light illumination test (Lx): 5000 ± 500 | Pink film-coated tablets, white after removal of the coating | — | Same as 0 d | Same as 0 d |
| | High humidity test: RH 75% | Pink film-coated tablets, white after removal of the coating | — | Same as 0 d | Same as 0 d |
| Example 17 | High temperature test (° C.): 60 ± 2 | Pink film-coated tablets, white after removal of the coating | Same as 0 d | Same as 0 d | Same as 0 d |
| | High temperature test (° C.): 40 ± 2 | Pink film-coated tablets, white after removal of the coating | Same as 0 d | Same as 0 d | Same as 0 d |
| | Intense light illumination test (Lx): 5000 ± 500 | Pink film-coated tablets, white after removal of the coating | Same as 0 d | Same as 0 d | Same as 0 d |
| | High humidity test: RH 75% | Pink film-coated tablets, white after removal of the coating | Same as 0 d | Same as 0 d | Same as 0 d |

Note:
"—" means not studied.

TABLE 11

Results of weight gain or loss assay

| Condition | Sample | Weight gain or loss (%) | Sample | Weight gain or loss (%) |
|---|---|---|---|---|
| High temperature 60° C. | Example 17-5 d | −0.8 | — | — |
| | Example 17-10 d | −0.1 | Lyrica ®CR-10 d | −1.7 |
| | Example 17-30 d | −0.9 | Lyrica ®CR-30 d | −1.7 |
| High temperature 40° C. | Example 17-5 d | −0.1 | — | — |
| | Example 17-10 d | −0.3 | Lyrica ®CR-10 d | −0.6 |
| | Example 17-30 d | −0.3 | Lyrica ®CR-30 d | −0.9 |

TABLE 11-continued

Results of weight gain or loss assay

| Condition | Sample | Weight gain or loss (%) | Sample | Weight gain or loss (%) |
|---|---|---|---|---|
| High temperature RH 75% | Example 17-5 d | 2.9 | — | — |
| | Example 17-10 d | 3.9 | Lyrica ®CR-10 d | 5.0 |
| | Example 17-30 d | 5.0 | Lyrica ®CR-30 d | 9.1 |
| Light illumination 5000LX | Example 17-5 d | 0.3 | — | — |
| | Example 17-10 d | 0.2 | Lyrica ®CR-10 d | 0.0 |
| | Example 17-30 d | 0.3 | Lyrica ®CR-30 d | −0.5 |

Note:
"—" means not studied.

TABLE 12

Results of dissolution study
Cumulative release of pregabalin sustained release tablets in 0.06N HCl (%)

| Sample | | 0 | 1 h | 2 h | 4 h | 8 h | 12 h | 16 h | 24 h | $f_2$ |
|---|---|---|---|---|---|---|---|---|---|---|
| Lyrica ® CR | 0 d | 18.8 | 30.0 | 45.7 | 66.7 | 79.7 | 88.2 | | 97.4 | 80 |
| Example 17 | | 19.0 | 29.6 | 43.9 | 63.3 | 76.3 | 85.8 | | 97.2 | |
| Lyrica ® CR | 40° C. 10 d | 19.2 | 30.7 | 46.7 | 67.8 | 81.1 | 89.5 | | 98.4 | 78 |
| Example 17 | | 18.7 | 29.1 | 43.8 | 63.8 | 78.0 | 88.4 | | 101.6 | |
| Lyrica ® CR | 40° C. 30 d | 19.2 | 30.9 | 47.6 | 70.2 | 84.3 | 93.3 | | 102.2 | 65 |
| Example 17 | | 18.7 | 29.1 | 43.5 | 63.2 | 77.7 | 87.9 | | 101.2 | |
| Lyrica ® CR | 60° C. 10 d | 19.3 | 30.7 | 46.9 | 68.1 | 81.4 | 89.8 | | 98.4 | 93 |
| Example 17 | | 19.5 | 30.6 | 46.3 | 67.8 | 82.1 | 91.8 | | 102.2 | |
| Lyrica ® CR | 60° C. 30 d | 19.8 | 31.1 | 47.5 | 69.0 | 82.1 | 90.5 | | 97.9 | 72 |
| Example 17 | | 19.9 | 30.1 | 44.0 | 63.4 | 77.8 | 87.9 | | 101.1 | |
| Lyrica ® CR | Light illumination 10 d | 19.8 | 31.3 | 47.7 | 69.6 | 83.3 | 91.8 | | 100.3 | 60 |
| Example 17 | | 18.5 | 28.9 | 42.8 | 61.4 | 74.1 | 83.3 | | 95.0 | |
| Lyrica ® CR | Light illumination 30 d | 19.2 | 30.8 | 47.3 | 69.2 | 82.8 | 92.2 | | 100.6 | 59 |
| Example 17 | | 18.5 | 28.6 | 42.4 | 60.9 | 73.6 | 83.0 | | 94.4 | |
| Lyrica ® CR | RH75% 10 d | 20.4 | 32.1 | 49.0 | 69.9 | 83.9 | 91.8 | | 100.7 | 65 |
| Example 17 | | 19.4 | 30.0 | 44.4 | 64.2 | 76.9 | 86.0 | | 95.6 | |
| Lyrica ® CR | RH75% 30 d | 18.9 | 30.2 | 46.1 | 67.1 | 80.1 | 89.2 | | 98.5 | 67 |
| Example 17 | | 18.6 | 28.7 | 42.4 | 61.1 | 73.8 | 83.3 | | 94.9 | |

TABLE 13

| Test Item | Sample | Impurities | 0 d | Light illumination 5000 LX 10 d | Light illumination 5000 LX 30 d | High humidity RH75% 10 d | High humidity RH75% 30 d | High temperature 40° C. 10 d | High temperature 40° C. 30 d | High temperature 60° C. 10 d | High temperature 60° C. 30 d |
|---|---|---|---|---|---|---|---|---|---|---|---|
| Related material | Example 17 | Degraded impurity C: | 0.08 | 0.08 | 0.08 | 0.06 | 0.06 | 0.12 | 0.19 | 0.52 | 1.08 |
| | | Maximum unknown impurity: | N.D. | N.D. | N.D. | N.D. | N.D. | N.D. | N.D. | N.D. | 0.33 |
| | | Total impurities: | 0.08 | 0.08 | 0.08 | 0.06 | 0.06 | 0.12 | 0.19 | 0.52 | 1.65 |
| | Lyrica ® CR | Degraded impurity C: | 0.31 | 0.27 | 0.27 | 0.26 | 0.26 | 0.32 | 0.38 | 0.89 | 1.67 |
| | | Maximum unknown impurity: | N.D. | N.D. | N.D. | N.D. | N.D. | N.D. | N.D. | N.D. | 0.48 |
| | | Total impurities: | 0.31 | 0.27 | 0.27 | 0.26 | 0.26 | 0.32 | 0.38 | 0.89 | 3.20 |

Note: Impurity C of 4-isobutylpyrrolidin-2-one is a degradation impurity of the active substance of pregabalin, with a molecular formula of $C_8H_{15}NO$, and molecular weight of 141.21. The structure is as follows:

TABLE 14

Results of content measurement

| Test Item | Sample | 0 d | Light illumination 5000 LX 10 d | Light illumination 5000 LX 30 d | High humidity RH75% 10 d | High humidity RH75% 30 d | High temperature 40° C. 10 d | High temperature 40° C. 30 d | High temperature 60° C. 10 d | High temperature 60° C. 30 d |
|---|---|---|---|---|---|---|---|---|---|---|
| Content (%) | Example 17 | 98.1 | 98.6 | 97.6 | 98.2 | 97.7 | 97.0 | 98.5 | 97.8 | 99.2 |
| | Lyrica ® CR | 100.0 | 98.7 | 98.7 | 99.2 | 98.7 | 97.4 | 98.5 | 98.0 | 98.4 |

The results of influencing factors test showed no significant change in appearance traits of the samples of Example 17 and Lyrica® CR was observed in 30 days under each condition. The pregabalin sustained release tablet was hygroscopic. The hygroscopic weight gain of Example 17 under high humidity (RH75%) condition is significantly lower than that of Lyrica® CR. That is, the hygroscopicity of the sample in Example 17 was significantly improved compared with Lyrica® CR. There was no significantly change in dissolution rate under each condition. The dissolution profile of Example 1⁷ was similar to that of Lyrica® CR. The degraded impurity C of pregbalin sustained release tablets increased under high temperature conditions. The samples in Example and Lyrica® CR increased significantly at 60° C., and Lyrica® CR increased more. That is, the stability of the sample in Example 17 was better.

In summary, the prepared tablet of Example 17 significantly more stable than that of Lyrica® CR according to the result of the stability.

Bioequivalence Test of Drug in Human Body
1. Purpose

A single oral administration of a control formulation of pregabalin sustained release tablet (R, LYRICA® CR, sustained release tablet, batch number T73417, specification 330 mg/tablet) and test formulation (T, Example 17, specification of 330 mg/tablet) were investigated to evaluate the bioequivalence thereof.

2. Instruments, Drugs and Agents
2.1 Instrument

| Name | Manufacturer | Device Number |
|---|---|---|
| Balance | MSA225S-CE, Sartorius, Germany | II 051-021 |
| Vortex mixer | Wiggens Vortex | II 050-477 |
| Multi-tube vortex oscillator | VX-II, Beijing Targin Technology Co., Ltd | II 050-490 |
| Desktop high speed refrigerated centrifuge | Sigma 3K15 | II 050-494 |

-continued

| Name | Manufacturer | Device Number |
|---|---|---|
| Desktop high speed refrigerated centrifuge | Sigma 3-18KS | II 050-693 |
| UPLC-MS/MS | ACQUITY UPLC H-class/ XEVO TQD, Waters | II 050-503 |
| Milli Q UltraPure Water System | MilliPore Advantage A10 | II 050-325 |

2.2 Drugs and Agents

| Name | Manufacturer | Batch Number |
|---|---|---|
| Pregabalin | NICPBP | 101106-201001 |
| Pregbalin-d4 | TLC | 2904-018A1 |
| Dimethyl sulfoxide | McLean | C10102428 |
| Methanol | Merck | I0953707 820 |
| Formic Acid | ROE | 5C2017 |
| Acetonitrile | Merck | JA050030 |
| Isopropanol | Merck | 1.01040.4008 |
| Blank, plasma of human | Purchased from Beijing Kemengda Technology Development Co., Ltd. | 180305 |

3. Sample Preparation

To 40 μL of unknown plasma sample, 40 μL of acetonitrile-water solution (1:1, v/v) and 40 μL of internal standard solution (pregabalin-d4 1000 ng·mL$^{-1}$) were added followed by 120 μL of methanol. The mixture obtained was vortexed for 2 min, centrifuging under 15000 rpm at 4° C. for 10 min. 50 μL of the supernatant was aspirated, added with 150 μL of 0.1% formic acid aqueous solution, and homogenously mixed. 5 μL was taken for LC-MS/MS quantitative analysis.

4. Test Result
4.1 Human Plasma Sample Test

Figure 3:
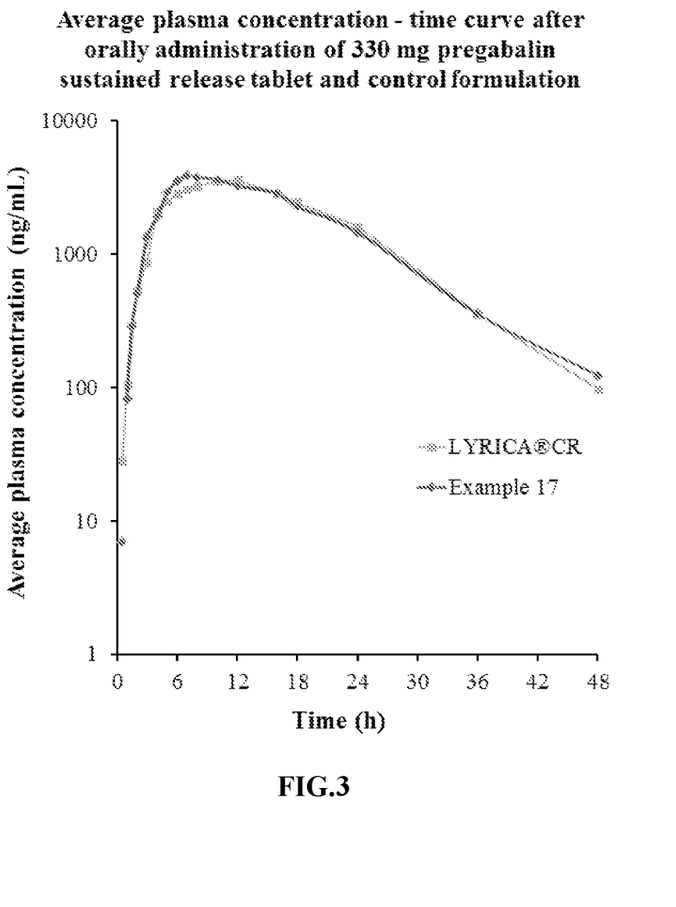
FIG. 3 is a graph showing a curve of the average drug concentration-time (Mean±standard deviation (SD)) for pregabalin in plasma, after a single oral administration of tested pregabalin sustained release tablet formulation (330 mg/tablet) and a control formulation of Lyrica® CR (330 mg/tablet) to a healthy person after meal.

The human plasma samples to be tested were divided into 6 batches for analysis. Each of the analyzed batch has a linear correlation coefficient greater than 0.9900. Each concentration point on the standard curve of pregabalin sustained release tablets of different batches has an average RE % within ±15%. FIG. 3 shows plasma drug concentration-time curve of a single orally administration after meal to a healthy subject for a tested pregabalin sustained release tablet formulation and control formulation.

4.2 Human Plasma Pharmacokinetic Parameters

After single orally administration after meal to a healthy subject of tested and control formulation of HPR, HPR has an average elimination half-life $t_{1/2}$ of 6.08±0.718 h and 6.08±1.05 h, respectively, an average peak time $T_{max}$ of 8.80±3.08 h and 9.90±3.35 h, respectively, an average $C_{max}$ of 4381±1107 ng·mL$^{-1}$ and 4370±870 ng·mL$^{-1}$, respectively, an average $AUC_{0\rightarrow 1}$ of 71361±12040 h·ng·mL$^{-1}$ and 72243=17132 h·ng·mL$^{-1}$, respectively, and an average $AUC_{0\rightarrow\infty}$ of 72053±12163 h·ng·mL$^{-1}$ and 73131±17371 h·ng·mL$^{-1}$, respectively.

4.3 Statistical Results of Human Plasma

For these two formulations, 90% confidence intervals of the ratios of $Ln(AUC_{0\rightarrow t})$, $Ln(AUC_{0\rightarrow\infty})$ and $Ln(C_{max})$ is 90.72%-111.45%, 90.39%-111.29% and 88.54%-110.80%, respectively. $T_{max}$ has a P value <0.05 by two-sided t test. The above results show that the two formulations are bioequivalent. Table 15 shows the statistical results of bioequivalence confidence interval for single orally administration of tested and control formulation after meal to a healthy person.

TABLE 15

| Parameter | Confidence interval | P Value |
|---|---|---|
| Ln ($C_{max}$) | 88.54~110.80 | — |
| Ln($AUC_{0\rightarrow t}$) | 90.72~111.45 | — |
| Ln($AUC_{0\rightarrow\infty}$) | 90.39~111.29 | — |
| Treatment|(SEQ1 = SEQ2) | — | 0.246 |
| Treatment & Residual (simultaneous) | — | 0.463 |

Note:
Equivalence determination standard of $AUC_{0-t}$, $AUC_{0-\infty}$ and $C_{max}$ 90% confidence interval: 80.00%-125.00%.
Equivalence determination standard of $T_{max}$: $p \geq 0.05$ The above examples are intended to illustrate substantial of the present application, rather than limit the scope thereof. A person skilled in the art should understand that the technical solutions of the present application may be modified or equivalently altered, without departing from the spirit and scope thereof.

The invention claimed is:

1. A pregabalin sustained release tablet comprising a pregabalin sustained release composition, wherein, based on the total weight of the pregabalin sustained release composition, the pregabalin sustained release composition comprises:
   (a) 25%-35% by weight of an active ingredient;
   (b) 15%-30% by weight of a matrix-forming agent;
   (c) 9%-29% by weight of a swelling agent;
   (d) 4%-14% by weight of a gelling agent; and
   (e) 15%-30% by weight of a filler;
   wherein, the active ingredient is pregabalin or a pharmaceutically acceptable salt or hydrate thereof,
   the swelling agent is polyoxyethylene,
   the filler is microcrystalline cellulose, or pregelatinized starch, or a combination thereof,
   the matrix-forming agent is a mixture of polyvinyl acetate and polyvinylpyrrolidone, and
   the gelling agent is carbomer, and
   the pregabalin sustained release tablet has a rigidity of 1909 gram force per millimeter or more at 6 hour after being subjected to a dissolution.

2. The pregabalin sustained release tablet according to claim 1, wherein the pregabalin or the pharmaceutically acceptable salt or hydrate thereof has a particle size $D_{90}$ of 250 to 600 μm.

3. The pregabalin sustained release tablet according to claim 1, wherein,
   the weight percentage of the active ingredient is 25%-30%;
   the weight percentage of the swelling agent is 9%-20%; and
   the weight percentage of the gelling agent is 4%40%, based on the total weight of the pregabalin sustained release composition.

4. The pregabalin sustained release tablet according to claim 1, wherein the composition further comprises a lubricant.

5. The pregabalin sustained release tablet according to claim 1, wherein the composition is coated with a coating powder.

6. A method for preparing the pregabalin sustained release composition as defined in claim 1 comprising:
   mixing the active ingredient, the matrix-forming agent, the swelling agent, the gelling agent, and the filler, and then subjecting the mixture to a shaping process.

7. The method for preparing the pregabalin sustained release composition according to claim 6, wherein the mixing time is 10-30 min.

8. The pregabalin sustained release tablet according to claim 4, wherein the lubricant is a constituent selected from the group consisting of magnesium stearate, talc powder, micropowder of silica gel, sodium stearyl fumarate, glyceryl behenate and polyethylene glycol, and a combination thereof.

9. The pregabalin sustained release tablet according to claim 4, wherein the weight percentage of the lubricant is 0.1%-1.5%, based on the total weight of the pregabalin sustained release composition.

10. The pregabalin sustained release tablet according to claim 5, wherein the coating powder comprises a constituent selected from the group consisting of:
    at least one of polyvinyl alcohol and polyethylene glycol,
    at least one of silica and talc powder,
    a flavoring agent, and
    a combination thereof.

11. The pregabalin sustained release tablet according to claim 5, wherein the weight percentage of the coating powder is 2%-6%, based on the total weight of the pregabalin sustained release composition.

* * * * *

UNITED STATES PATENT AND TRADEMARK OFFICE
CERTIFICATE OF CORRECTION

PATENT NO. : 11,938,222 B2
APPLICATION NO. : 16/618756
DATED : March 26, 2024
INVENTOR(S) : Zhu et al.

Page 1 of 1

It is certified that error appears in the above-identified patent and that said Letters Patent is hereby corrected as shown below:

In the Specification

In Column 23, Table 11 under Condition:
Delete "High temperature RH 75%" and insert --High humidity RH 75%--;

In the Claims

Column 28, Line 19, in Claim 3:
Delete "4%40%" and enter --4%-10%--.

Signed and Sealed this
Twenty-first Day of May, 2024

Katherine Kelly Vidal
*Director of the United States Patent and Trademark Office*